United States Patent [19]
Zadeh

[11] Patent Number: 5,336,242
[45] Date of Patent: Aug. 9, 1994

[54] BAND-PASS FILTER FOR USE IN A SENSE AMPLIFIER OF AN IMPLANTABLE CARDIAC PACER

[75] Inventor: Ali E. Zadeh, Sierra Madre, Calif.

[73] Assignee: Siemens Pacesetter, Inc., Sylmar, Calif.

[21] Appl. No.: 67,367

[22] Filed: May 26, 1993

[51] Int. Cl.$^5$ .............................. A61N 1/365
[52] U.S. Cl. .............................. 607/11; 607/9
[58] Field of Search .............. 607/11, 17, 18, 25, 607/26, 4, 5, 9

[56] References Cited

U.S. PATENT DOCUMENTS

| | | | |
|---|---|---|---|
| 4,000,461 | 12/1976 | Barber et al. | 324/102 |
| 4,458,692 | 7/1984 | Simson | 128/705 |
| 4,556,062 | 12/1985 | Grassi et al. | 607/26 |
| 4,596,255 | 6/1986 | Snell et al. | 128/697 |
| 4,712,555 | 12/1987 | Thornander et al. | 607/17 |
| 4,817,605 | 4/1989 | Sholder | 607/28 |
| 4,940,052 | 7/1990 | Mann et al. | 607/17 |
| 4,964,406 | 10/1990 | Carroll et al. | 607/5 |
| 4,969,462 | 11/1990 | Callaghan et al. | 67/26 |
| 4,972,835 | 11/1990 | Caroll et al. | 607/4 |
| 4,989,602 | 2/1991 | Sholder et al. | 607/4 |
| 5,010,887 | 4/1991 | Thornander | 128/696 |

OTHER PUBLICATIONS

Millman & Grabel, *Microelectronics*, 2d ed., McGraw Hill, pp. 728–751 (1987).

Jong, *Methods of Discrete Signal and System Analysis*, McGraw Hill, pp. 346–363 (1982).

Markus, *Modern Electronic Circuits Reference Manual*, McGraw Hill, p. 313 (1980).

*Primary Examiner*—Angela D. Sykes
*Assistant Examiner*—George Manuel
*Attorney, Agent, or Firm*—Bryant R. Gold; Malcolm J. Romano

[57] ABSTRACT

A low-power band-pass filter for use in a cardiac pacer includes a single operational amplifier connected in circuit relationship with a plurality of switched capacitors that function as bilinear resistors. Each bilinear resistor comprises a switch for coupling a first lead of a capacitive element to a first terminal and for coupling a second lead of the capacitive element to a second terminal in response to a first state of a control signal, and for coupling the first lead of the capacitive element to the second terminal and for coupling the second lead of the capacitive element to the first terminal in response to a second state of the control signal. Thus, the bilinear resistor switches or oscillates the electrical orientation of the capacitive element between the first terminal and the second terminal in response to the first and second states of the control signal. The invention also includes a method of operating such an implantable filter circuit. Such method includes the steps of: (a) oscillating periodically the electrical orientation of the capacitive element of each bilinear resistor in a prescribed manner; while (b) applying an input signal to the band-pass filter circuit while such oscillation occurs.

21 Claims, 5 Drawing Sheets

BAND-PASS FILTER FOR USE IN A SENSE AMPLIFIER OF AN IMPLANTABLE CARDIAC PACER

BACKGROUND OF THE INVENTION

1. Field of the Invention

The present invention relates to cardiac event detection. More particularly, the present invention relates to a lower power, active band-pass filter circuit, and filtration method for use within an implantable cardiac pacer.

The major pumping chambers in the human heart are the left and right ventricles. The simultaneous physical contraction of the myocardial tissue in these chambers expels blood into the aorta and the pulmonary artery. Blood enters the ventricles from smaller antechambers called the left and right atria which contract about 100 milliseconds (ms) before the ventricles. The physical contractions of the muscle tissue result from the depolarization of such tissue, which depolarization is induced by a wave of spontaneous electrical excitation which begins in the sinus node of the right atrium, spreads to the left atrium and then enters what is known as the AV node which delays its passage to the ventricles via the so-called bundle of His. The frequency of the waves of excitation is normally regulated metabolically by the sinus node. The atrial rate is thus referred to as the sinus rate or sinus rhythm of the heart.

Electrical signals corresponding to the depolarization of the myocardial muscle tissue appear in the patient's electrocardiogram. A brief low amplitude signal, commonly referred to as the P-wave, accompanies atrial depolarization. The P-wave is normally followed by a much larger amplitude signal, known as the QRS complex, with a predominant R-wave signifying ventricular depolarization. Repolarization prior to the next contraction is marked by a broad waveform in the electrocardiogram known as the T-wave.

A typical implanted cardiac pacer (or pacemaker) operates by supplying missing stimulation pulses through an electrode on a pacing lead in contact with the atrial or ventricular muscle tissue. The electrical stimulus independently initiates depolarization of the myocardial (atrial or ventricular) tissue resulting in the desired contraction. The P-wave or R-wave can be sensed through the same lead, i.e., the pacing lead, and used as a timing signal to synchronize or inhibit stimulation pulses in relation to spontaneous (natural or intrinsic) cardiac activity. The sensed signals are referred to as an atrial electrogram or ventricular electrogram respectively.

Every modern-day implantable pacemaker includes a sensing circuit, whether the activity of one or both chambers of the heart are sensed. When the electrical signal of the atrial or ventricular electrogram is transmitted from the heart into the pacemaker, the electrical signal is typically passed through an amplifier, referred to as the sense amplifier. The sense amplifier serves two primary functions: (1) it amplifies the incoming electrogram electrical signal so that such signal (which may only be 0.1 to 10 millivolts (mV) when received) may be processed and detected more accurately; and (2) it filters the incoming electrogram signal to eliminate "noise" and other unwanted components that may be contained therein, e.g., the low frequency T-wave. Noise is commonly introduced into the electrogram signal from sources outside the body, e.g., florescent lighting, or inside the body, e.g., electrical signals in the muscles of the chest.

Typically, the sense amplifier is able to substantially filter out such noise and other unwanted components so as to provide a relatively "clean" amplified electrical signal to the other electronic circuits, e.g., a window detector and/or an analog-to-digital (A/D) converter, of the cardiac pacer. Unfortunately, however, the typical band-pass filter circuits used in cardiac pacing applications require two operational amplifiers, one for a high-pass stage and the other for a low-pass stage. Such two stage filters provide second order filtration and achieve generally favorable results. However, the amount of power consumed by these two stage filters is disadvantageously high, thereby increasing the demand on the implanted pacer's battery and, as a result, decreasing the battery's lifespan.

The internal circuits of an implantable pacer are typically integrated into a single integrated circuit or "chip." These integrated circuits have the advantage of being much smaller than similar circuits constructed either partially or completely from discrete components. The sense amplifier is one of the most important parts of such integrated circuit because for the pacemaker to operate properly, it must be able to accurately and reliably sense the incoming electrogram signal. For dual chamber pacemakers, two sense amplifiers on the integrated circuit are required, one for processing the incoming electrogram signal from the atrium, and the other for processing the incoming electrogram signal from the ventricle. At least one of these sense amplifiers should stay alert all of the time to continuously monitor the heart for the occurrence of electrogram signals. Hence, the power consumption of the sense amplifier that must be alert all of the time becomes a critical design parameter that can significantly affect the life of the pacemaker battery.

Further, because sense amplifiers must monitor, amplify, filter, and process electrogram electrical signals that are very small is magnitude (on the order of 0.1–10 mV), such sense amplifiers must be low noise circuits, meaning that any noise generated or picked up by such sense amplifiers should be less than about 0.1 mV. Disadvantageously, if the sense amplifier is not a low noise circuit, then the noise from the sense amplifier corrupts the incoming electrogram signal and makes it useless for further processing.

In theory, the realization of the band-pass filter function within a sense amplifier may be achieved in various ways. First, a passive filter, i.e., a filter comprising only passive components (such as resistors and capacitors) may be utilized. Advantageously, a passive filter is very low noise (i.e., it generates noise components having a magnitude on the order of only 10 $\mu v$ to 100 $\mu v$). However, a passive filter circuit is simply not acceptable for use within a pacemaker because it does not amplify the signal. To the contrary, a passive filter attenuates the incoming signal.

Second, an active band-pass filter made from discrete components could be utilized. While discrete active band-pass filter circuits may be designed as very low noise circuits, such circuits are also not acceptable for use within a pacemaker. Their power consumption is too high, and they occupy too much space. Further, because they must be made from components mounted on a hybrid substrate, their use adversely impacts the reliability and manufacturability of the pacemaker.

Third, an active band-pass filter circuit made as an integrated part of the pacemaker's circuit chip may be utilized. Such approach is the preferred approach for implantable pacemakers because it occupies less space (area) on the integrated circuit chip, and consumes less power. However, because such circuits share a common substrate with all of the other circuits within the pacemaker, they tend to be somewhat noisier than other active filter circuits.

Therefore, improvements are needed in the filter circuits used in sense amplifiers of cardiac pacers.

SUMMARY OF THE INVENTION

The present invention advantageously provides an improved filter circuit for use in sense amplifiers of cardiac pacers. Specifically, the present invention provides an improved low-power band-pass filter for use in a cardiac pacer. Advantageously, the filter circuit of the present invention is realizable in integrated circuit technology, and achieves improved performance in terms of reduced power consumption, reduced noise, and reduced chip area. In one embodiment of the invention, a single operational amplifier is utilized in combination with switched capacitors (or bilinear resistors) to realize the desired filter circuit.

The present invention may thus be characterized, in accordance with one embodiment thereof, as an implantable cardiac pacer that includes: (1) a first connection point through which an input signal (e.g., the electrogram signal) can be received by the cardiac pacer, and a second connection point through which a therapeutic output signal (e.g., a stimulation pulse) can be delivered by the cardiac pacer; (2) a pace amplifier coupled to the second connection point so as to deliver the therapeutic output signal to the second connection point; (3) a pacing controller, coupled to the pace amplifier, that initiates the pace amplifier generated therapeutic output signal; and (4) a sense amplifier coupled between the pacing controller and the first connection point, so as to receive the input signal from the first connection point. Note, as is common in the pacer art, the first and second connection points may comprise a single common connection point.

The sense amplifier that forms part of the invention includes a band-pass filter circuit. Such filter circuit may be characterized as a network including: (1) a first bilinear resistor coupled between a terminal (A) and a terminal (B), wherein the terminal (A) is coupled to the first connection point; (2) a first capacitor that is coupled between the terminal (B) and a terminal (C); (3) a second capacitor that is coupled between the terminal (B) and a terminal (D), wherein the terminal (D) is coupled to the pacing controller; (4) a second bilinear resistor that is coupled between the terminal (C) and the terminal (D); and (5) an operational amplifier with an inverting input that is coupled to the terminal (C), a non-inverting input that is coupled to analog ground, and an output that is coupled to the terminal (D). (Note, as used herein, "analog ground" is a dc reference voltage that lies somewhere on or between the power supply rails that supply power to the pacemaker circuits. In a pacemaker, the positive (+) power supply terminal is usually considered as ground, and the negative (−) power supply terminal is considered as the supply voltage. Where the negative supply is −2.8 v., the "analog ground" is typically around −0.5 v.)

In accordance with the invention, each of the bilinear resistors may also be characterized as a network. The first bilinear resistor, for example, includes a first switching means for coupling a first lead of a first capacitive element to the terminal (A) and for coupling a second lead of the first capacitive element to the terminal (B) in response to a first state of at least one control signal, and for coupling the first lead of the first capacitive element to the terminal (B) and for coupling second lead of the first capacitive element to the terminal (A) in response to a second state of the at least one control signal. Thus, the electrical orientation of the first capacitive element can be oscillated relative to the terminal (A) and the terminal (B) in response to the first and second states. The second bilinear resistor similarly comprises a second switching means and a second capacitive element, but is coupled between the terminal (C) and the terminal (D).

More specifically, the first bilinear resistor may be characterized as an "H" network including: (1) a first switching element coupled between the terminal (A) and a terminal (E); (2) a second switching element coupled between the terminal (E) and the terminal (B); (3) a third switching element coupled between the terminal (A) and a terminal (F); (4) a fourth switching element coupled between the terminal (F) and the terminal (B); with the first capacitive element being coupled between the terminal (E) and the terminal (F). Thus, the first and second switching elements comprise the upper and lower left-hand vertical legs of the "H", respectively, the third and fourth switching elements comprise the upper and lower right-hand vertical legs of the "H", respectively, and the first capacitive element comprises the horizontal member of the "H". A first control signal is coupled to the first and fourth switching elements and a second control signal is coupled to the second and third switching elements. The control signals each have an asserted (on) state and a not-asserted (off) state and are non-overlapping. As used herein the term "non-overlapping" means that the second control signal is in its not-asserted (off) state whenever the first control signal is in its asserted (on) state, and the first control signal is in its not-asserted (off) state whenever the second control signal is in its asserted (on) state. In other words, the first and second control signals are never asserted (on) simultaneously, however it is contemplated that the signals could be not-asserted (off) simultaneously.

The second bilinear resistor may also be characterized as an "H" network that is substantially similar to the first bilinear resistor.

Another embodiment of the present invention may be viewed as a method of operating the bilinear resistors (specifically the switching means of the bilinear resistors) of the above-mentioned sense amplifier of an implantable pacer. Such method includes, e.g., the steps of: (a) oscillating periodically the electrical orientation of the capacitive elements of the bilinear resistors in a prescribed manner; and (b) applying the cardiac (or electrogram) signal to the band-pass filter circuit while such oscillating is occurring. The oscillating step is carried out by: (1) asserting (turning on) the first control signal; (2) maintaining such assertion for a first predetermined period of time; (3) not-asserting (turning off) the first control signal at the end of the first predetermined period of time and asserting (turning on) the second control signal; (4) maintaining the second control signal in its asserted state for a second predetermined period of time; (5) not-asserting (turning off) the second control signal at the end of the second predetermined period of time; and (6) repeating steps (1) through (5) for as long as operation of the band-pass filter is desired. In a preferred implementation, the predetermined period of time is equal to one half of a phase (or sampling) period ($T_s$). For practical reasons, the sampling period ($T_s$) comprises the reciprocal of a sampling frequency ($f_s$) which is at least 8 to 10 times greater than the upper bandedge frequency of the band-pass filter circuit network.

It is thus a feature of the present invention to provide improved band-pass filtration in a cardiac pacer.

A further feature of the present invention is to provide a low-power band-pass filter circuit for use in a cardiac pacer.

Another feature of the invention is to provide a low-noise band-pass filter circuit.

An additional feature of the invention is to realize such improved band-pass filter circuit using switching means, capacitors and no more than one operational-amplifier.

Yet another feature of the invention is to provide such an improved band-pass filter where the switching means, capacitors, and operational amplifier are realized using solid state integrated circuit technology.

Yet a further feature of the invention is to provide a band-pass filter circuit that, when implemented as part of an integrated circuit chip on a silicon substrate, occupies less space on the silicon substrate than has heretofore been possible.

Still another feature of the invention is to provide such an improved band-pass filter circuit on a single integrated circuit chip.

DESCRIPTION OF THE DRAWINGS

The above and other aspects, features and advantages of the present invention will be more apparent from the following more particular description thereof, presented in conjunction with the following drawings wherein like numbers have been used to refer to substantially identical elements.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
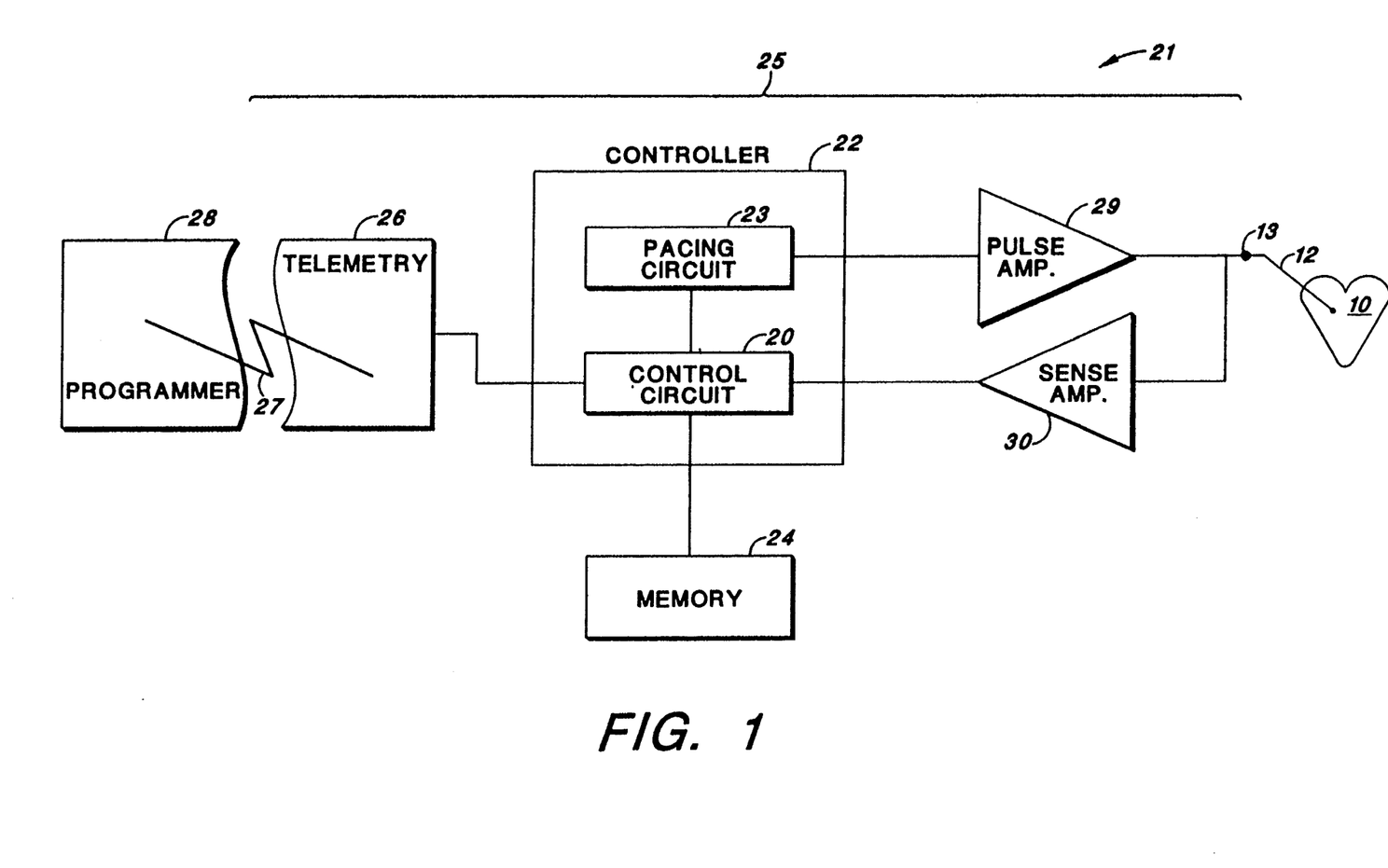
FIG. 1 is a block diagram of a cardiac pacer.

Referring to FIG. 1, a block diagram is shown of a cardiac pacer (or cardiac pacing system) 21. The cardiac pacing system 21 comprises an implantable device 25 that is implanted into a patient and coupled to a heart 10 of the patient via an electrogram lead 12. The electrogram lead 12 provides electrical communication between the implantable device 25 and the heart 10. The lead 12 is coupled to the device 25 at a connection point 13. The connection point 13 may be a detachable coupling wherein the electrogram lead 12 may be coupled to and decoupled from the implantable device 25. One signal that is communicated through the electrogram lead 12 from the heart 10 to the implantable device 25 is an electrogram (or input) signal, which electrogram signal evidences cardiac activity (i.e., depolarization of the atria and/or ventricles), or the absence of cardiac activity. The implantable device 25 is housed in an implantable, hermetically sealed housing (not shown) as is known in the art of implantable electronic pacemakers.

The cardiac pacer 21 includes a pacing controller 22, comprised of a pacing circuit 23 and a control circuit 20; a memory circuit 24; a telemetry circuit 26; a pulse amplifier 29; and a sense amplifier 30.

The pulse amplifier 29 and the sense amplifier 30 are coupled to the electrogram or pacing lead 12. Generally, the pacing lead 12 will be the same lead i.e., a single common lead as is shown in FIG. 1. Accordingly, the connection point 13 is generally a single coupling between the lead 12 and the implantable device 25. However, it is contemplated that the lead 12 may be two or more separate leads. As a result, the electrogram lead 12 may, e.g., be coupled to the first connection point and be used for sensing, and another lead, used for pacing, may be coupled to a second connection point. For purposes of illustration, the configuration of FIG. 1 is assumed to include only a single lead 12 and a single connection point 13, which single lead serves both to communicate the electrogram or input signal to the implantable device 25, and to communicate the stimulation pulse or the therapeutic output signal to the heart 10.

The pulse amplifier 29 is also coupled to the pacing circuit 23. The pacing circuit 23 initiates the therapy, i.e., the therapeutic output signal, delivered to the heart by the pulse amplifier 29 via the pacing lead 12. The pacing circuit 23 operates in response to the control circuit 20, which determines the appropriate therapy to deliver to the heart.

In determining what is optimum therapy, the control circuit 20 may use a memory 24. Various control parameters may be stored in the memory 24 by a physician using a telemetry circuit 26, which is also coupled to the control circuit 20. In order to store such parameters, the physician utilizes an external (non-implanted) programmer 28 that is coupled to the control circuit 20 via the telemetry circuit 26. A suitable non-invasive communication link 27, e.g., capacitive or inductive coupling is established between the programmer 28 and the telemetry circuit 26 as is known in the art.

The control circuit 20 is also coupled to the sense amplifier 30. One function of the sense amplifier 30 is to filter the incoming electrogram signal from the heart 10 so as to eliminate "noise" and other unwanted components of the electrogram signal, e.g., the low frequency T-wave. Noise is commonly introduced into the electrogram signal from sources outside the body, e.g., fluorescent lighting, or sources inside the body, e.g., electrical signals in the muscles of the chest. By way of example, the sense amplifier may operate over a passband of 20 to 120 Hz; have a center frequency ($\omega_o$) of approximately 40–50 Hz, a quality factor ($Q_o$) of approximately 0.3 to 0.4, and a mid-band gain ($H_o$) of 2 to 5. Preferably, the sense amplifier should be very low power; low noise, and should be realizable in switched capacitor integrated circuit technology. The function of the sense amplifier 30 is thus to receive and preliminarily process (filter and amplify) the incoming electrogram signal so that the output signal generated by the sense amplifier provides the control circuit with a true indication of the cardiac activity.

By way of definition, it is noted that when a filter operates over a passband ranging from a low frequency $f_1$ to a high frequency $f_2$, where both $f_1$ and $f_2$ are expressed in Hz (cycles per second), the low frequency $f_1$ is commonly referred to as the lower bandedge, $\omega_L$, where $\omega_L = 2\pi f_1$; and the high frequency $f_2$ is commonly referred to as the upper bandedge, $\omega_U$, where $\omega_U = 2\pi f_2$. In such instance, the center frequency is expressed as $\omega_0 = 2\pi f_0$, where $f_0$ is the center frequency expressed in Hz. As is known in the filter design art, the relationship between the bandedges, $\omega_L$, $\omega_U$, the quality factor $Q_0$, and the center frequency $\omega_0$ is as follows:

$$\text{upperbandedge} = \omega_U = \frac{\omega_o}{2Q_o}(1 + \sqrt{1 - 4Q_o^2})$$

$$\text{lowerbandedge} = \omega_L = \frac{\omega_o}{2Q_o}(1 - \sqrt{1 - 4Q_o^2})$$

from which it is seen that $$\omega_o = \sqrt{\omega_U \omega_L}$$

The control circuit 20 receives the output signal from the sense amplifier 30 and, in response thereto, evaluates whether or not optimum therapy is being delivered to the heart 10, based on both the output signal and the parameters stored in the memory 24. If the therapy being delivered is not optimum, the control circuit 20 makes adjustments, as required, to the pacing circuit 23. In response to the adjustments, the pacing circuit 23 begins delivering a more optimum therapy to the heart 10 via the pulse amplifier 29.

Note that if noise or other undesirable components of the electrogram signal are not filtered out of the electrogram signal by the sense amplifier, or if the sense amplifier itself is a noisy circuit (i.e., if it generates noise components on its own that are excessive), the control circuit will make erroneous adjustments to the therapy delivered by the pacing circuit. Such erroneous adjustments could be injurious to the person or animal wherein the cardiac pacing system is implanted.

Alternatively, various therapy circuits other than the pacing circuit 23 may be utilized with the cardiac pacer 21 of the present invention, such as stimulators, implantable electrical defibrillators, implantable monitoring devices, and the like.

The pulse amplifier 29, controller 22 (including the pacing circuit 23 and control circuit 20), memory 24, telemetry circuit 26, and programmer 28 may be of conventional design, as is shown, e.g., in U.S. Pat. Nos. 4,596,255; 4,712,555; 4,817,605; and 4,940,052; incorporated herein by reference. The present invention relates primarily to improvements in the sense amplifier 30.

Figure 2:
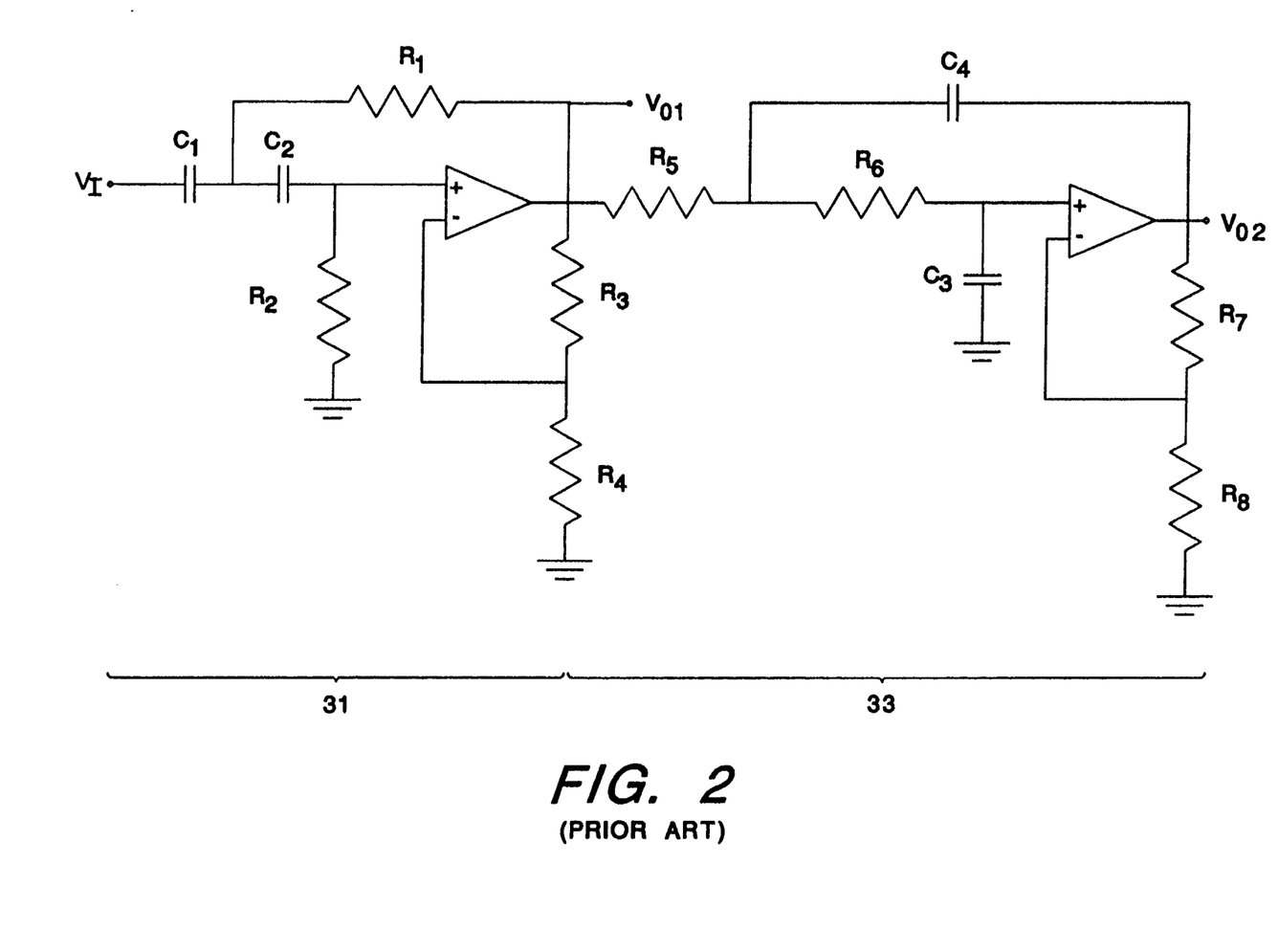
FIG. 2 is schematic diagram of a prior art, two-stage, band-pass filter that has heretofore been used in conjunction with the cardiac pacer of FIG. 1.

Referring next to FIG. 2, a two-stage band-pass filter of the prior art is shown. Such two-stage (i.e., a filter using two operational amplifiers) has heretofore been used as the sense amplifier 30 in most implantable pacemakers. A high-pass stage 31 and a low-pass stage 33 are used to achieve two functions: (1) high-pass and (2) band-pass, so as to realize the desired band-pass filter characteristics. As seen in FIG. 2, $V_I$ is the input signal. The output signal of the high-pass stage 31 is a signal $V_{01}$. That is, $V_{01}$ is the output of the high-pass stage with respect to the input $V_I$, and the transfer function $V_{01}/V_I$ thus provides the desired high-pass filter characteristic. However, the signal $V_{01}$ is also the input to the low-pass stage 33. The output signal of the low-pass stage 33 is a signal $V_{02}$. The transfer function $V_{02}/V_I$ (which is equal to $V_{02}/V_{01} \times V_{01}/V_I$) thus provides the desired band-pass filter characteristic, with the high-pass stage 31 defining the lower bandedge, and the low-pass stage 33 defining the upper bandedge. As configured, it is generally less sensitive to component variations, and it is thus ideal for high Q (i.e., Q>10) communication electronic circuits, such as voice or video signal processing and filtering. Significantly, however, these advantages are not applicable to a cardiac pacer. In a cardiac pacer, only the band-pass function is needed. Further, since the intracardiac signal tends to be very broadband, a low Q filter is all that is needed. Additionally, the two-stage filter carries numerous disadvantages for a pacer application. The two-stage filter, for example, requires two operational amplifiers and therefore consumes approximately twice the power consumed by a single operational amplifier filter. Moreover, using two stages requires twice as many components, which typically translates to a requirement of twice as much chip area as does a single stage device. Also, using two stages creates a problem relative to the amplification of the input noise that is present at the first stage. Hence, it is evident that the advantages of the two-stage filter design are outweighed by the disadvantages of such design when the filter is to be used within a cardiac pacer.

Figure 3:
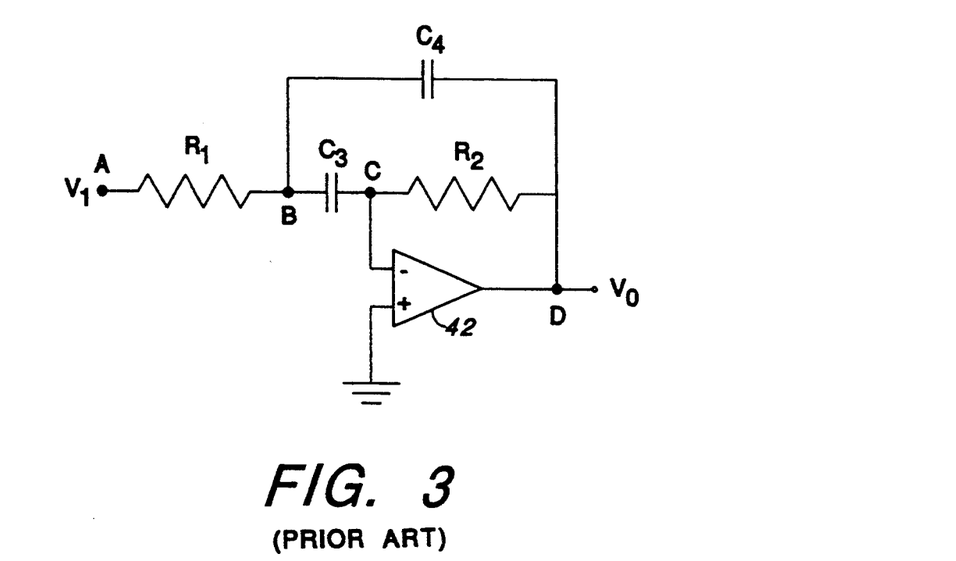
FIG. 3 is a schematic diagram of a "Friend" biquadratic filter circuit.

Turning next to FIG. 3, a multiple feedback band-pass, or "Friend", biquadratic filter is shown Filters of the type shown in FIG. 3 are constructed using two capacitors $C_3$, $C_4$, two resistors $R_1$, $R_2$ and a single operational amplifier 42. The operational amplifier 42 is in a first parallel combination with a resistor $R_2$, coupled between the inverting input of the amplifier 42 and its output. The non-inverting input of the amplifier 42 is coupled to analog ground. One end of the first parallel combination (amplifier 42 in parallel with the resistor $R_2$) is connected in a first series combination with a first lead of a capacitor $C_3$, which first lead is also coupled to the inverting input of the amplifier 42. The first series combination (comprising the amplifier 42/resistor $R_2$ in series with the capacitor $C_3$) is connected in a second parallel combination with a capacitor $C_4$. The capacitor $C_4$ is thus connected between a second lead of the first capacitor $C_3$ and the output of the amplifier 42. Finally, the second parallel combination (comprising amplifier 42/resistor $R_2$ in series with $C_3$ in parallel with $C_4$) is coupled in a series combination with a resistor $R_1$. That is, a first lead of the resistor $R_1$ is coupled to the second lead of the first capacitor $C_3$, and a second lead of the second resistor $R_1$ serves as an input terminal to which an input signal, $V_I$, may be coupled to the Friend filter. The output of the amplifier 42 serves as an output $V_o$ of the Friend filter.

Advantageously, the filter circuit shown in FIG. 3 provides band-pass filtration and may be characterized by the following transfer function:

$$\frac{V_o}{V_I}(s) = H(s) =$$

$$\frac{-\left(\frac{1}{R_1 C_4}\right)s}{s^2 + \left(\frac{1}{R_2 C_3} + \frac{1}{R_2 C_4}\right)s + \left(\frac{1}{R_1 R_2 C_3 C_4}\right)}$$

$$= \frac{-H_0 \left(\frac{\omega_0}{Q_0}\right)s}{s^2 + \left(\frac{\omega_0}{Q_0}\right)s + \omega_0^2}$$

where $H(s)$ is the transfer function, s is a complex continuous input frequency, $R_1$ and $R_2$ are the resistance values of the resistors $R_1$ and $R_2$ respectively, $C_3$ and $C_4$ are the capacitance values of the capacitors $C_3$ and $C_4$ respectively, $\omega_o$ is the center frequency of the filter circuit, $H_o$ is the gain of the filter circuit at the center frequency, and $Q_o$ is the quality factor of the filter circuit.

The filter circuit of FIG. 3 advantageously provides band-pass filtration using a single operational amplifier, thereby reducing power consumption. The center frequency quality factor and mid-band gain of the filter circuit of FIG. 3 are characterized as follows:

Center Frequency, $\omega_0 = \frac{1}{\sqrt{R_1 R_2 C_3 C_4}}$

Quality Factor, $Q_0 = \sqrt{\frac{C_3 C_4}{C_3 + C_4}} \sqrt{\frac{R_2}{R_1}}$

Mid-Band Gain, $H_0 = \left(\frac{R_2}{R_1}\right)\left(\frac{C_3}{C_3 + C_4}\right)$ As mentioned above, in the typical cardiac pacing application, the following filter characteristics are desirable:

a center frequency $\omega_o$ of $\approx 40$–$50$ Hz,
a quality factor $Q_o$ of $\approx 0.3$–$0.4$,
a mid-band gain $H_o \approx 2$–$5$.

These filter characteristics can be achieved by choosing $R_1 = R$, $C_3 = C$, $R_2 = \alpha R$, and $C_4 = \beta C$. Then:

$$\omega_0 = \frac{1}{\sqrt{\alpha \beta}} \cdot \frac{1}{RC}$$

$$Q_0 = \frac{\sqrt{\alpha \beta}}{(\beta + 1)}$$

$$H_0 = \frac{\alpha}{(\beta + 1)}$$

Using the desired center frequency ($\omega_o$), quality factor ($Q_o$), and mid-band gain ($H_o$), the resistors $R_1$, $R_2$ and capacitors $C_3$, $C_4$ can be characterized as follows:

$$C_3 = C$$

$$C_4 = \left(\frac{Q_0^2}{H_0 - Q_0^2}\right) C$$

$$R_1 = \frac{1}{\omega_0} \left(\frac{H_0 - Q_0^2}{H_0 Q_0}\right) \frac{1}{C}$$

$$R_2 = \frac{1}{\omega_0} \left(\frac{H_0}{Q_0}\right) \frac{1}{C}$$

Thus, if C is chosen to be a size that can readily be realized in integrated circuit technology, e.g., 20 pf; and $Q_o = 0.35$, $H_o = 2$ and $\omega_o = 2\pi \times 50$; then $C_3 = 20$ pf, $C_4 = 1.305$ pf, $R_1 = 426.9$ MΩ, and $R_2 = 909.5$ MΩ. Hence, in order to achieve the desired filter characteristics and, at the same time, for the capacitors $C_3$, $C_4$ to be large enough to be realizable in integrated circuit technology (0.1 to 50 pf), the resistors $R_1$ and $R_2$ must be chosen to have large resistance values (on the order of 100's of MΩ). However, because the Friend filter requires such large resistance values for $R_1$ and $R_2$, and because such large resistance values are difficult, if not impossible, to realize using integrated circuit technology, the use of the otherwise desirable Friend filter has heretofore been precluded in implantable devices, such as cardiac pacemakers.

Figure 4:
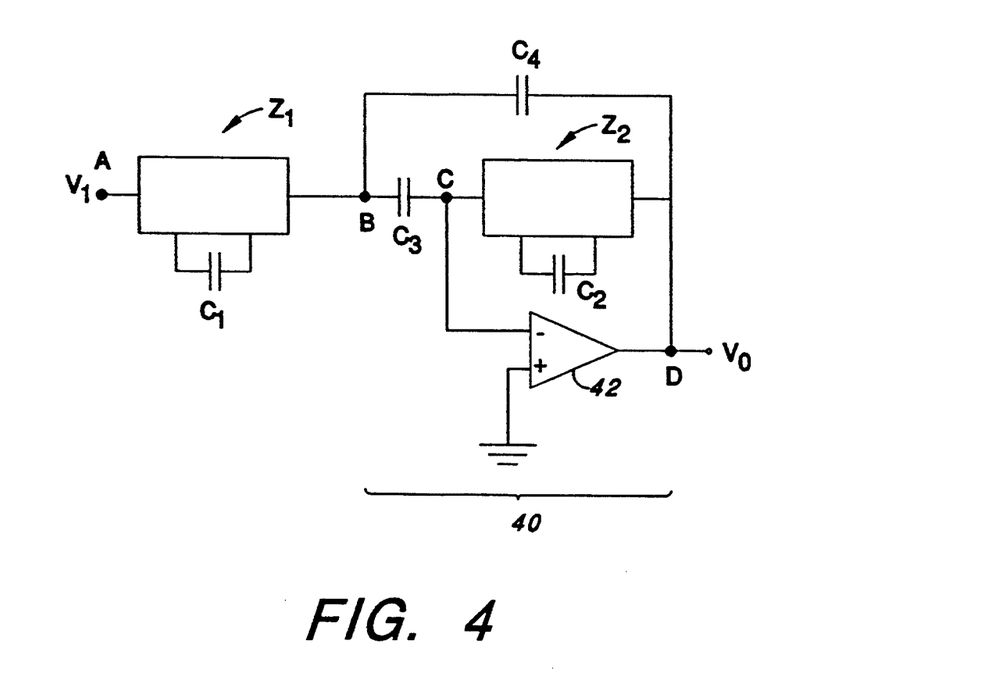
FIG. 4 is a schematic diagram of one embodiment of a filter circuit made in accordance with the present invention, which filter circuit emulates the Friend biquadratic filter of FIG. 3.

Referring next to FIG. 4, a switched capacitor or bilinear resistor approximation of the Friend filter of FIG. 3 is shown. A first switched capacitor or bilinear resistor $Z_1$ is coupled in series between an input terminal (A), to which the input signal $V_I$ is applied, and an active network 40. The network 40 is coupled to an output terminal (D), at which the output signal $V_o$ appears. The active network 40 is comprised of: an operational amplifier 42 in a parallel combination with a second switched capacitor or bilinear resistor $Z_2$, with $Z_2$ being connected between the inverting input of the operational amplifier 42 and its output (D); the non-inverting input of the operational amplifier is coupled to analog ground; the parallel combination (the operational amplifier 42 in parallel with $Z_2$) is connected in series with a first capacitor $C_3$ at the inverting input of the operational amplifier (terminal (C)); the series combination resulting from such series connection is connected in parallel with a second capacitor $C_4$, which capacitor $C_4$ is coupled to the first switched capacitor $Z_I$ at the same point, terminal (B), where the two capacitors $C_3$, $C_4$ connect; and the output of the operational amplifier is coupled to the output terminal (D).

Each of the bilinear resistors $Z_1$ and $Z_2$ comprises a switching means for coupling a first lead of a capacitive element ($C_1$ or $C_2$) to a first terminal of the bilinear resistor and for coupling a second lead of the capacitive element to a second terminal of the bilinear resistor in response to a first state of at least one control signal, and for coupling the first lead of the capacitive element to the second terminal of the bilinear resistor and for coupling the second lead of the capacitive element to the first terminal of the bilinear resistor in response to a second state of the at least one control signal. Thus, the bilinear resistors function so as to oscillate or switch back and forth the electrical orientation of the capacitive element in response to the first and second states of the at least one control signal. The capacitive element of the bilinear resistor $Z_1$ is shown in FIG. 4 as $C_1$; and the capacitive element of the bilinear resistor $Z_2$ is shown in FIG. 4 as $C_2$.

In operation, the electrical orientation of the capacitors $C_1$, $C_2$ is oscillated periodically at a sampling frequency, described below, so as to cause the switched capacitor equivalent circuit to a approximate the Friend filter of FIG. 4, as described more completely hereinbelow. The electrogram signal or cardiac signal received from the electrogram lead 12 is applied to the switched capacitor equivalent circuit so as to produce an output signal that approximates the output of a Friend filter circuit.

Figure 5:
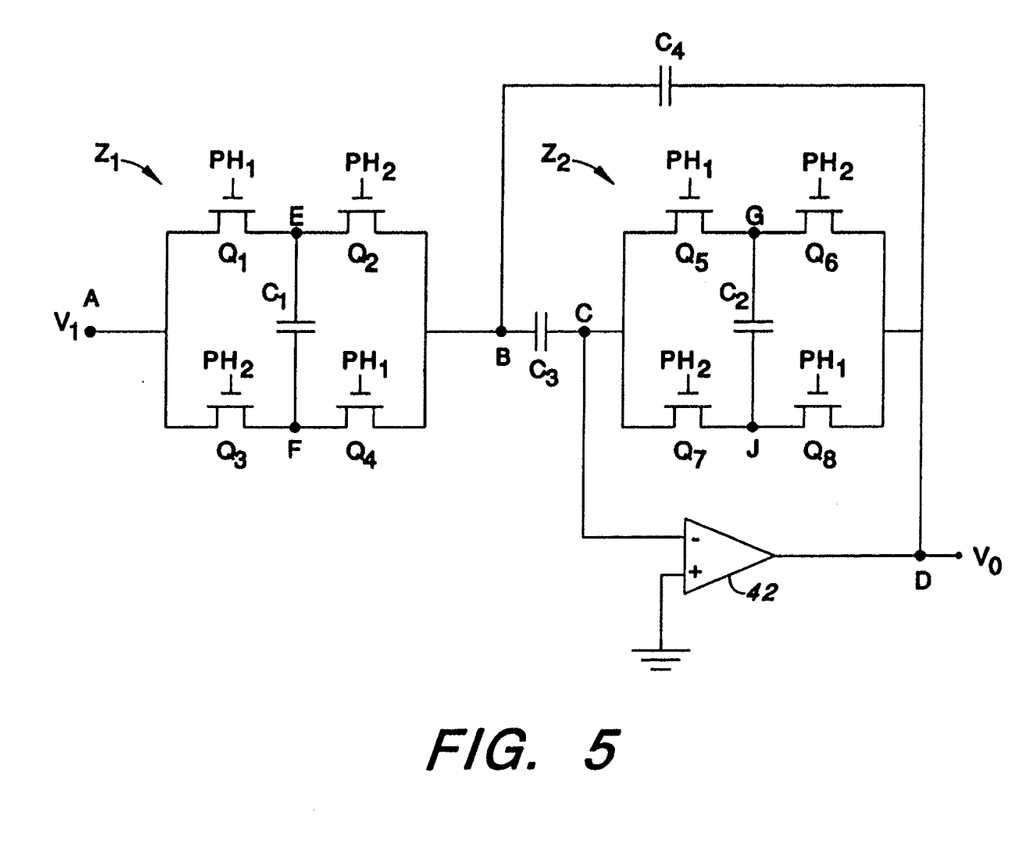
FIG. 5 is a detailed schematic diagram of the embodiment of the invention shown in FIG. 4.

Referring next to FIG. 5, the switched capacitor equivalent circuit of FIG. 4 is shown with one embodiment of the first and second switched capacitors. The switched capacitors $Z_1$, $Z_2$ are realized using two "H" configuration networks wherein four solid state switching devices $Q_1$, $Q_2$, $Q_3$, $Q_4$, or $Q_5$, $Q_6$, $Q_7$, $Q_8$ make up the "vertical legs" of each of the "H's", and a capacitor $C_1$, or $C_2$ makes up the "cross piece" or "horizontal member" of each of the "H's". In FIG. 5, two switching devices $Q_1$, $Q_4$ or $Q_5$, $Q_8$ at opposite corners of the "H" are controlled by a first control signal $PH_1$, having an asserted state (on) and a not-asserted state (off), and the other two switching devices $Q_2$, $Q_3$ or $Q_6$, $Q_7$ are controlled by a second control signal $PH_2$ also having an asserted state (on) and a not-asserted state (off). The control signals $PH_1$, $PH_2$ are non-overlapping and are realized as is known in the art.

Figure 6:
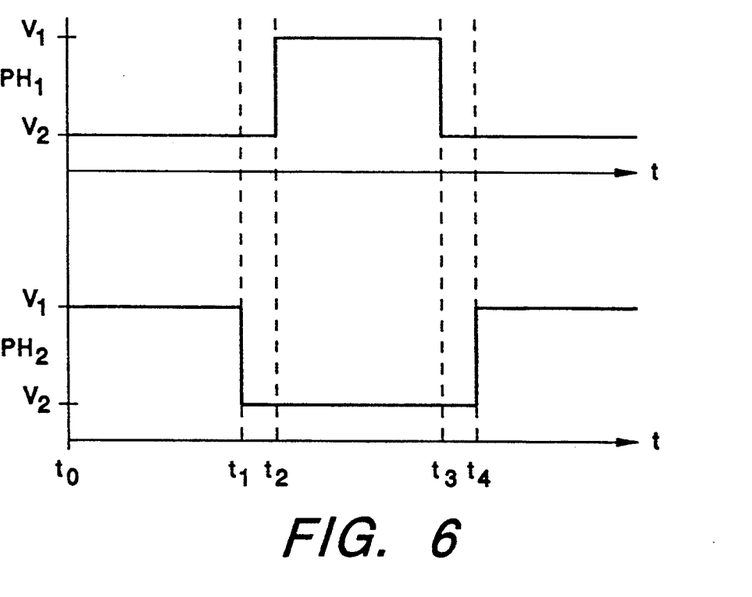
FIG. 6 is a timing diagram showing a non-overlapping relationship between a first control signal $PH_1$ and a second control signal $PH_2$ used in the operation of the embodiment of the present invention shown in FIG. 5.

As used herein, the term "non-overlapping" means that the second control signal is in its not-asserted state (off) whenever the first control signal is in its asserted state (on), and the first control signal is in its not-asserted (off) state whenever the second control signal is in its asserted state (on). In other words, the first and second control signals are never asserted (on) simultaneously, however it is contemplated that the signals could be not-asserted (off) simultaneously. An example of the control signals $PH_1$, $PH_2$ is shown in FIG. 6 wherein the asserted state (on) is represented as $V_1$ and the not-asserted state (off) is represented as $V_2$. Specifically, FIG. 6 illustrates the first control signal $PH_1$ as not-asserted $V_2$ (illustrated on the vertical or voltage axis) at time $t_0$ (illustrated on the horizontal or time axis) and illustrates the second control signal $PH_2$ as asserted $V_1$ at time $t_0$. At time $t_1$, the second control signal $PH_2$ becomes not-asserted $V_2$ and the first control signal remains not-asserted $V_2$. Then, at time $t_2$, the first control signal $PH_1$ becomes asserted $V_1$ and remains asserted $V_1$ until time $t_3$ when it becomes not-asserted $V_2$ again. Finally, at time $t_4$, the second control signal $PH_2$ becomes asserted $V_1$ again. Thus, the control signals $PH_1$, $PH_2$ are shown as non-overlapping signals.

Referring again to FIG. 5, when the first control signal $PH_1$ is asserted (on) (and the second control signal $PH_2$ is not-asserted (off)), a first and second lead of the capacitors $C_1$, $C_2$ is connected to a first and second terminal respectively of the switched capacitors $Z_1$, $Z_2$. (The term asserted (on) is used to designate the control signal state that turns the switching devices $Q_1$ through $Q_8$ on, and the term not-asserted (off) is used to designate the control signal state that turns the switching devices $Q_1$ through $Q_8$ off.) Similarly, when the first control signal $PH_1$ is not-asserted (off) (and the second control signal $PH_2$ is asserted (on)), a first and second lead of the capacitors $C_1$, $C_2$ is connected to the second and first terminal of the switched capacitors, respectively. Thus, the electrical orientation of the capacitors $C_1$, $C_2$ can be oscillated relative to the first and second terminals of the switched capacitors in response to the first and second control signals being either asserted (on) or not-asserted (off).

Advantageously, by implementing the Friend filter, using switched capacitors or bilinear resistors $Z_1$, $Z_2$, the advantages of the Friend filter can be realized without the concomitant disadvantage of large resistors (on the order of 100's of M$\Omega$).

Using the bilinear resistors $Z_1$, $Z_2$ the continuous active RC Friend filter of FIG. 3 can be transformed to a switched capacitor equivalent circuit as shown in FIG. 5, characterized by the following transfer function:

$$H(s) = \frac{-H_0 \left(\frac{\omega_0}{Q_0}\right)s}{s^2 + \left(\frac{\omega_0}{Q_0}\right)s + \omega_0^2} \quad \text{where } s = \frac{2}{T_s} \cdot \frac{1 - z^{-1}}{1 + z^{+1}}$$

and $$f_s = \frac{1}{T_s} = \text{Sampling Frequency} \approx 2048,$$

and $$H(z) = \frac{-H_0 \left(\frac{2\omega_0 T_s}{4Q_0 + 2\omega_0 T_s + \omega_0^2 T_s^2 Q_0}\right)(z^2 - 1)}{z^2 - 2\left(\frac{4Q_0 - \omega_0^2 T_s^2 Q_0}{4Q_0 + 2\omega_0 T_s + \omega_0^2 T_s^2 Q_0}\right)z + \left(\frac{4Q_0 - 2\omega_0 T_s + \omega_0^2 T_s^2 Q_0}{4Q_0 + 2\omega_0 T_s + \omega_0^2 T_s^2 Q_0}\right)},$$

where H(S) is the transfer function, s is a complex continuous input frequency, H(z) is a discrete transfer function, z is a complex discrete frequency, $\omega_o$ is the center frequency of the filter circuit, $H_o$ is the gain of the filter circuit at the center frequency, $Q_o$ is the quality factor of the filter circuit, and $T_5$ is the sampling period as defined by the sampling frequency above.

Figure 7:
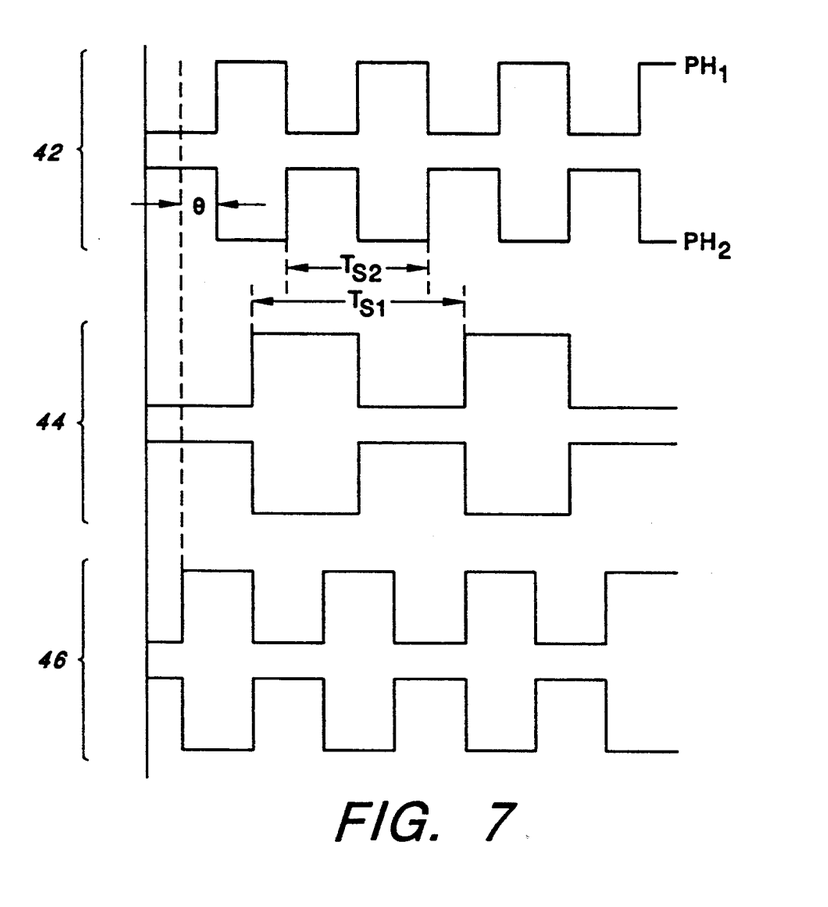
FIG. 7 is a timing diagram showing exemplary frequency and phase relationships between the control signals used in the present invention shown in FIG. 5.

The sampling frequency is the frequency of the first and second control signals when the first and second control signals are non-overlapping square-wave signals. Note however, referring to FIG. 7, that it is possible to use a set of control signals 42 of a first sampling frequency ($1/T_{s1}$) to control the first switched capacitor and a set of control signals 44 of a second sampling frequency ($1/T_{s2}$) to control the second switched capacitor. Similarly, the set of control signals 42 used to control the first switched capacitor may be out of phase or phase shifted (e.g., by θ degrees, where θ is between +90° and −90°), as the terms are used in the art, with respect to the set of control signals 46 used to control the second switched capacitor. However, in the embodiment of FIG. 5, the first and second control signals 42 are assumed to control both the first and second switched capacitors such that the control signals controlling the first and second switched capacitors are of the same frequency and are in phase with each other.

The bilinear transformation of the filter circuit transfer function warps the frequency response of the filter from continuous to discrete domain, and relationship between the continuous frequency $\omega_2$, and the discrete frequency $\omega_d$ is:

$$\omega_d = \frac{2}{T_s} \cdot \tan^{-1}\left(\frac{\omega_a}{2} T_s\right)$$

This suggests that if the frequency $$f_a\left(= \frac{\omega_a}{2\pi}\right)$$

of the signal $V_I$ is much less than the sampling frequency $$f_s\left(= \frac{\omega_s}{2\pi}\right),$$

the continuous frequency $f_a$ is approximately the same as the discrete frequency $$f_d\left(= \frac{\omega_d}{2\pi}\right).$$

Thus, for a typical sense amplifier in a cardiac pacing system, where:
Center Frequency $f_o \approx 50$ Hz
Sampling Frequency fhd s≈2048 Hz,
then:

$$\omega_o \text{ (center freq.)} = 2\pi \times 50 \rightarrow \omega_d = 2\pi \times 0.998 \times 50,$$

which shows that the error between $\omega_d$ and $\omega_a$, at $\omega_o$ (50 Hz) is about 0.2%; and $$\omega_2 \text{ (max. QRS freq.)} = 2\pi \times 120$$
$$\rightarrow \omega_d = 2\pi \times 0.968 \times 120,$$

which shows that the error between $\omega_d$ and $\omega_2$ at the maximum QRS frequency of about 120 Hz is about 1.1%. Thus, the filter circuit of the present invention (FIGS. 4 & 5) approximates the advantageous Friend filter circuit shown in FIG. 3, but does so without using the large resistors $R_1$ and $R_2$ that are required in the Friend filter circuit of FIG. 3.

By way of example, if $C_3$ is arbitrarily selected as C, then the capacitors $C_1$, $C_2$, and $C_4$ are characterized as follows:

$$C_1 = \frac{2\pi f_0}{4f_s}\left(\frac{H_0 Q_0}{H_0 - Q_0^2}\right) \cdot C$$

$$C_2 = \frac{2\pi f_0}{4f_s}\left(\frac{Q_0}{H_0}\right) \cdot C$$

$$C_4 = \left(\frac{Q_0^2}{H_0 - Q_0^2}\right) \cdot C$$

Thus, for the typical sense amplifier (broad-band, high sampling rate, and low midband gain) $C_3 = C >> C_1$, $C_2$, and $C_4$. For example, if $f_o = 50$ Hz, $Q_o = 0.35$, $H_o = 2$, $f_s = 2048$ Hz, and $C = 20$ pf, then:

$$C_3 = 20 pF$$

$$C_1 = \frac{2\pi \times 50}{4 \times 2048}\left(\frac{2 \times 0.35}{2 - (0.35)^2}\right) \times 20 \text{ pF} = (1.430 \times 10^{-2})(20 \text{ pF})$$
$$= 0.286 \text{ pF}$$

$$C_2 = \frac{2\pi \times 50}{4 \times 2048}\left(\frac{0.35}{2}\right) \times 20 \text{ pF} = (6.711 \times 10^{-3})(20 \text{ pF})$$
$$= 0.1342 \text{ pF}$$

$$C_4 = \left(\frac{(0.35)^2}{2 - (0.35)^2}\right) \times 20 \text{ pF} = (0.06525)(20 \text{ pF})$$
$$= 1.305 \text{ pF}$$

Note that, because $C_2$ will always be the smallest capacitor, in cardiac pacing system applications, C should be selected to be large enough so that $C_2$ can be readily realized in integrated circuit technology.

Thus, because the filter of the present invention utilizes one operational amplifier and does not require large discrete resistors to perform both high-pass and low-pass operations in a band-pass filter circuit, the present invention can be used both to improve the power consumption and noise generation of sense amplifiers used in cardiac pacing applications.

As explained above, FIG. 6 shows a timing diagram of a non-overlapping relationship between a first control signal $PH_1$ and a second control signal $PH_2$ wherein the asserted state (on) is represented as $V_1$ (illustrated on the vertical or voltage axis) and the not-asserted state (off) is represented as $V_2$. A method of utilizing or operating the apparatus of FIG. 5 includes (a) oscillating the orientation of the first and second capacitive elements $C_1$, $C_2$ in response to the control signals $PH_1$, $PH_2$, while (b) applying the electrogram or cardiac signal to the band-pass filter circuit at an input terminal (A) (FIG. 5).

In order to oscillate the orientation of the capacitive elements $C_1$, $C_2$, the first control signal $PH_1$ is applied to the first, fourth, fifth and eighth switching elements $Q_1$, $Q_4Q_5$, $Q_8$, and the second control signal $PH_2$ is applied to the second, third, sixth and seventh switching elements $Q_2$, $Q_3$, $Q_6$, $Q_7$.

At time $t_0$ (illustrated on the horizontal or time axis of FIG. 6), the control signal $PH_1$ is not asserted $V_2$ (off). At time $t_2$, the first control signal $PH_1$ becomes asserted $V_1$ (on) and remains asserted $V_1$ (on) for a first predetermined period of time, i.e., from $t_2$ to $t_3$, after which, at time $t_3$, the first control signal becomes not asserted $V_2$ (off) again. Preferably, the first control signal remains not asserted $V_2$ (off) for the first predetermined period of time after which it becomes asserted $V_1$ again. In operation, this process of asserting (turning on) and not asserting (turning off) the first control signal $PH_1$ is continuously repeated. As a result of asserting $V_1$ (turning on) the first control signal $PH_1$, the first, fourth, fifth and eighth switching elements $Q_1$, $Q_4$, $Q_5$, $Q_8$ are turned on, as described above; as a result of not asserting $V_2$ (turning off) the first control signal $PH_1$, the first, fourth, fifth and eighth switching elements $Q_1$, $Q_4$, $Q_5$, $Q_8$ are turned off, as described above.

Similarly, the second control signal $PH_2$ is asserted $V_1$ (on) at time $t_0$, and becomes not asserted $V_2$ (off) at time $t_1$. The second control signal $PH_2$ remains not asserted $V_2$ (off) for a second predetermined period of time, i.e., from $t_1$ to $t_4$, after which, at time $t_4$, the second control signal $PH_1$ becomes asserted $V_1$ (on) again. The second control signal $PH_2$ preferably remains asserted $V_1$ (on) for the second predetermined period of time. As with the first control signal, this process of asserting (turning on) an not asserting (turning off) the second control signal is continuously repeated. As a result of asserting $V_1$ (turning on) the second control signal $PH_2$, the second, third, sixth and seventh switching elements $Q_2$, $Q_3$, $Q_6$, $Q_7$ are turned on, as described above; as a result of not asserting $V_2$ (turning off) the second control signal $PH_2$, the second, third, sixth and eighth switching elements $Q_2$, $Q_3$, $Q_6$, $Q_7$ are turned off, as described above.

Note that for the particular control signals illustrated in FIG. 6, there is a first dwell period of time from $t_1$ to $t_2$, and a second dwell period of time from $t_3$ to $t_4$, where both control signals may be not asserted $V_2$ (off). In a preferred embodiment, however, the times $t_1$ and $t_2$ are preferably the same time, e.g., $t_a$, and $t_3$ and $t_4$ are preferably the same time, e.g., $t_b$. In other words, in a preferred embodiment, the first and second dwell periods of time are of zero duration. As a result, in the preferred method of operation, the first control signal $PH_1$ is asserted $V_1$ (on) whenever the second control signal $PH_2$ is not asserted $V_2$ (off) and vice versa. In addition, the first predetermined period of time is preferably of the same duration as the second predetermined period of time.

While the invention described herein has been described with reference to a particular embodiment and application thereof, numerous variations and modifications could be made thereto by those skilled in the art without departing from the spirit and scope of the invention as claimed. Accordingly, the scope of the invention should be determined with reference to the claims set forth below.

What is claimed is:

1. An implantable cardiac pacer for delivering therapy to a heart, said cardiac pacer comprising:
    a first connection point through which an input signal can be received by said cardiac pacer;
    a second connection point through which a therapeutic output signal can be delivered by said cardiac pacer;
    a pace amplifier coupled to the second connection point so as to deliver the therapeutic output signal to the second connection point;
    a pacing controller, coupled to the pace amplifier, that causes the pace amplifier to generate therapeutic output signal;
    a sense amplifier coupled between the pacing controller and the first connection point that receives the input signal from the first connection point;
    said sense amplifier including a band-pass filter circuit comprising:
        a first bilinear resistor coupled between a terminal (A) and a terminal (B), said terminal (A) being coupled to the first connection point,
        a first capacitor that is coupled between the terminal (B) and a terminal (C),
        a second capacitor that is coupled between the terminal (B) and a terminal (D), said terminal (D) being coupled to the pacing controller,
        a second bilinear resistor that is coupled between the terminal (C) and the terminal (D),
        an operational amplifier with an inverting input that is coupled to the terminal (C), a non-inverting input that is coupled to analog ground, and an output that is coupled to the terminal (D),
    said first bilinear resistor comprising a switching means for coupling a first lead of a first capacitive element to said terminal (A) and for coupling a second lead of the first capacitive element to said terminal (B) in response to a first state of at least one control signal, and for coupling the first lead of the first capacitive element to terminal (B) and for coupling second lead of the first capacitive element to terminal (A) in response to a second state of the at least one control signal, whereby the electrical orientation of the first capacitive element can be oscillated relative to the terminal (A) and the terminal (B) in response to said first and second states.

2. The implantable cardiac pacer of claim 1, wherein said first and second connection points comprise the same connection point.

3. The implantable cardiac pacer of claim 1, wherein:
    said first bilinear resistor comprises an "H" network including:
    a first switching element coupled between said terminal (A) and a terminal (E),
    a second switching element coupled between the terminal (E) and said terminal (B),
    a third switching element coupled between said terminal (A) and a terminal (F),
    a fourth switching element coupled between the terminal (F) and said terminal (B), and
    said first capacitive element coupled between the terminal (E) and the terminal (F),
    whereby first and second switching elements comprise the upper and lower left-hand vertical legs of the "H", respectively, the third and fourth switching elements comprise the upper and lower right-hand vertical legs of the "H", respectively, and the first capacitive element comprises the horizontal member of the "H";
    a first control signal coupled to the first and fourth switching elements, said first control signal having an asserted state and a not-asserted state; and
    a second control signal coupled to the second and third switching elements, second control signal also having an asserted state and a not-asserted state;
    said second control signal being non-overlapping with the first control signal in that the first and second control signals are never in their respective asserted states at the same time.

4. The implantable cardiac pacer of claim 3, wherein said second bilinear resistor comprises a switching means for coupling a first lead of a second capacitive element to said terminal (C) and for coupling a second lead of the second capacitive element to said terminal (D) in response to the first state of the at least one control signal, and for coupling the first lead of the second capacitive element to terminal (D) and for coupling second lead of the second capacitive element to terminal (C) in response to the second state of the at least one control signal, whereby the electrical orientation of the second capacitive element relative to the terminal (C) and the terminal (D) can be oscillated in response to said first and second states.

5. The implantable cardiac pacer of claim 4, wherein:
said second bilinear resistor comprises an "H" network including:
a fifth switching element coupled between said terminal (C) and a terminal (G),
a sixth switching element in series with the fifth switching element, coupled between the terminal (G) and said terminal (D),
a seventh switching element coupled between said terminal (C) and a terminal (J),
an eighth switching element in series with the seventh switching element, coupled between the terminal (J) and said terminal (D),
said second capacitive element coupled between the terminal (G) and the terminal (J),
whereby fifth and sixth switching elements comprise the upper and lower left-hand vertical legs of the "H", respectively, the seventh and eighth switching elements comprise the upper and lower right-hand vertical legs of the "H", respectively, and the second capacitive element comprises the horizontal member of the "H";
a third control signal coupled to the fifth and eighth switching elements, said third control signal having an asserted state and a not-asserted state; and
a fourth control signal coupled to the sixth and seventh switching elements, said fourth control signal also having an asserted state and a not-asserted state;
said fourth control signal being non-overlapping with the third control signal in that the third and fourth control signals are never in their respective asserted states at the same time.

6. The implantable cardiac pacer of claim 5, wherein said first, second, third and fourth control signals are periodic signals of a predetermined sampling frequency.

7. The implantable cardiac pacer of claim 6, wherein said first and second control signals are phase shifted between $-90°$ and $+90°$ relative to said third and fourth control signals.

8. The implantable cardiac pacer of claim 5, wherein:
said first and second control signals are of a first predetermined frequency; and
said third and fourth control signals are of a second predetermined frequency.

9. The implantable cardiac pacer of claim 5, wherein:
said first and third control signals comprise a first periodic signal; and said second and fourth control signals comprise a second periodic signal.

10. The implantable cardiac pacer of claim 9, wherein a discrete transfer function of said band-pass filter circuit comprises:

$$H(z) = \frac{-H_0 \left( \frac{2\omega_0 T_s}{4Q_0 + 2\omega_0 T_s + \omega_0^2 T_s^2 Q_0} \right)(z^2 - 1)}{z^2 - 2\left( \frac{4Q_0 - \omega_0^2 T_s^2 Q_0}{4Q_0 + 2\omega_0 T_s + \omega_0^2 T_s^2 Q_0} \right)z + \left( \frac{4Q_0 - 2\omega_0 T_s + \omega_0^2 T_s^2 Q_0}{4Q_0 + 2\omega_0 T_s + \omega_0^2 T_s^2 Q_0} \right)}$$

wherein $H(z)$ is the discrete transfer function, $z$ represents a complex discrete input frequency, $\omega_0$ is a center frequency of said band-pass filter circuit, $Q_0$ is a quality factor of said band-pass filter circuit, $H_0$ is a gain of said band-pass filter circuit at said center frequency, and $T_s$ is a sampling period of said control signals.

11. The implantable cardiac pacer of claim 10, wherein:
said sampling period ($T_s$) is no more than two milliseconds;
said quality factor ($Q_0$) is between 0.1 and 0.6; and
said center frequency ($\omega_0$) is between 25 Hz and 75 Hz.

12. The implantable cardiac pacer of claim 11, wherein:
said sampling period ($T_s$) is approximately 0.488 milliseconds;
said quality factor ($Q_0$) is approximately 0.35; and
said center frequency ($\omega_0$) is approximately 50 Hz.

13. The implantable cardiac pacer of claim 10, wherein said second capacitive element has a capacitance less than said first capacitive element.

14. The implantable cardiac pacer of claim 13, wherein said second capacitive element is a capacitor of at least 0.1 pf.

15. In an implantable pacing system for delivering electrical therapy to a heart, a method of filtering an electrogram signal received from the heart, said implantable cardiac pacer including a band-pass filter circuit for filtering the cardiac signal, said band-pass filter circuit having a center frequency and including a switching means for coupling a first lead of a capacitor to a first terminal and for coupling a second lead of the capacitor to a second terminal in response to a first state of at least one control signal, and for coupling the first lead of the capacitor to the second terminal and for coupling the second lead of the capacitor to the first terminal in response to a second state of the at least one control signal, whereby the electrical orientation of the capacitor can be oscillated with respect to the first and second terminals in response to said first and second states, said method comprising:
(a) oscillating periodically the electrical orientation of the capacitor in a prescribed manner; while
(b) applying the electrogram signal to the band-pass filter circuit.

16. The method of claim 15, wherein said oscillating step includes:
(1) applying said at least one control signal having said first state to said switching means; then
(2) waiting a predetermined period of time, said predetermined period of time being equal to one half of a phase period wherein the phase period being equal to said sampling period ($T_s$); then (3) changing the state of the at least one control signal to said second state and applying said at least one control signal to said switching means; then (4) waiting the predetermined period of time; then (5) changing the state of the at least one control signal to said first state; and (6) repeating steps (1) through (5).

17. An filter circuit comprising:

a first bilinear resistor coupled between a terminal (A) and a terminal (B), a first capacitor that is coupled between the terminal (B) and a terminal (C), a second capacitor that is coupled between the terminal (B) and a terminal (D), a second bilinear resistor that is coupled between the terminal (C) and the terminal (D), and an operational amplifier with an inverting input that is coupled to the terminal (C), a non-inverting input that is coupled to ground, and an output that is coupled to the terminal (D)

said first bilinear resistor comprising a switching means for coupling a first lead of a first capacitive element to said terminal (A) and for coupling a second lead of the first capacitive element to said terminal (B) in response to a first state of at least one control signal, and for coupling the first lead of the first capacitive element to terminal (B) and for coupling second lead of the first capacitive element to terminal (A) in response to a second state of the at least one control signal, whereby the electrical orientation of the first capacitive element can be oscillated relative to the terminal (A) and the terminal (B) in response to said first and second states; and said second bilinear resistor comprising a switching means for coupling a first lead of a second capacitive element to said terminal (C) and for coupling a second lead of the second capacitive element to said terminal (D) in response to the first state of the at least one control signal, and for coupling the first lead of the second capacitive element to terminal (D) and for coupling second lead of the second capacitive element to terminal (C) in response to the second state of the at least one control signal, whereby the electrical orientation of the second capacitive element relative to the terminal (C) and the terminal (D) can be oscillated in response to said first and second states.

18. The filter circuit of claim 17, wherein:

said first bilinear resistor comprises an "H" network including:

a first switching element coupled between said terminal (A) and a terminal (E), a second switching element coupled between the terminal (E) and said terminal (B), a third switching element coupled between said terminal (A) and a terminal (F), a fourth switching element coupled between the terminal (F) and said terminal (B), said first capacitive element coupled between the terminal (E) and the terminal (F);

said second bilinear resistor comprises an "H" network including:

a fifth switching element coupled between said terminal (C) and a terminal (G), a sixth switching element coupled between the terminal (G) and said terminal (D), a seventh switching element coupled between said terminal (C) and a terminal (J), an eighth switching element coupled between the terminal (J) and said terminal (D), and said second capacitive element coupled between the terminal (G) and the terminal (J);

a first control signal coupled to the first and fourth switching elements;

a second control signal coupled to the second and third switching elements;

said second control signal being non-overlapping with the first control signal in that the first and second control signals never turn on the switching elements to which they are respectively connected at the same time;

a third control signal coupled to the fifth and eighth switching elements; and a fourth control signal coupled to the sixth and seventh switching elements;

said fourth control signal being non-overlapping with the third control signal in that the third and fourth control signals never turn on the switching elements to which they are respectively connected at the same time.

19. The filter circuit of claim 17, wherein said first and third control signals comprise a first periodic signal;

said second and fourth control signals comprise a second periodic signal; and a discrete transfer function of said band-pass filter circuit is expressed as:

$$H(z) = \frac{-H_0\left(\frac{2\omega_0 T_s}{4Q_0 + 2\omega_0 T_s + \omega_0^2 T_s^2 Q_0}\right)(z^2 - 1)}{z^2 - 2\left(\frac{4Q_0 - \omega_0^2 T_s^2 Q_0}{4Q_0 + 2\omega_0 T_s + \omega_0^2 T_s^2 Q_0}\right)z + \left(\frac{4Q_0 - 2\omega_0 T_s + \omega_0^2 T_s^2 Q_0}{4Q_0 + 2\omega_0 T_s + \omega_0^2 T_s^2 Q_0}\right)}$$

wherein H(z) is the discrete transfer function, z represents a complex discrete input frequency, $\omega_o$ is a center frequency of said band-pass filter circuit, $Q_o$ is a quality factor of said band-pass filter circuit, $H_o$ is a gain of said band-pass filter circuit at said center frequency and $T_s$ is a sampling period of said control signals.

20. An implantable cardiac pacer for delivering therapy to a heart, said cardiac pacer comprising:

a first connection point through which an input signal can be received by said cardiac pacer;

a second connection point through which a therapeutic output signal can be delivered by said cardiac pacer;

a pace amplifier coupled to the second connection point so as to deliver the therapeutic output signal to the second connection point;

a pacing controller, coupled to the pace amplifier, that causes the pace amplifier to generate therapeutic output signal;

a sense amplifier coupled between the pacing controller and the first connection point that receives the input signal from the first connection point;

said sense amplifier including a band-pass filter circuit comprising:
- a first bilinear switched capacitor resistor coupled between a terminal (A) and a terminal (B), said terminal (A) being coupled to the first connection point,
- a first capacitor that is coupled between the terminal (B) and a terminal (C),
- a second capacitor that is coupled between the terminal (B) and a terminal (D), said terminal (D) being coupled to the pacing controller,
- a second bilinear switched capacitor resistor that is coupled between the terminal (C) and the terminal (D),
- an operational amplifier with an inverting input that is coupled to the terminal (C), a non-inverting input that is coupled to analog ground, and an output that is coupled to the terminal (D).

21. An filter circuit comprising:
- a first bilinear switched capacitor resistor coupled between a terminal (A), and a terminal (B),
- a first capacitor that is coupled between the terminal (B) and a terminal (C),
- a second capacitor that is coupled between the terminal (B) and a terminal (D),
- a second bilinear switched capacitor resistor that is coupled between the terminal (C) and the terminal (D), and
- an operational amplifier with an inverting input that is coupled to the terminal (C), a non-inverting input that is coupled to ground, and an output that is coupled to the terminal (D).

* * * * *